United States Patent [19]

Schaar

[11] 4,378,800

[45] * Apr. 5, 1983

[54] DISPOSABLE DIAPER

[75] Inventor: Charles H. Schaar, Lake Zurich, Ill.

[73] Assignee: Colgate-Palmolive Company, New York, N.Y.

[ * ] Notice: The portion of the term of this patent subsequent to Jul. 18, 1995, has been disclaimed.

[21] Appl. No.: 769,547

[22] Filed: Feb. 17, 1977

Related U.S. Application Data

[62] Division of Ser. No. 410,375, Oct. 29, 1973, Pat. No. 4,100,921.

[51] Int. Cl.³ .............................................. A61F 13/16
[52] U.S. Cl. .................................................. 604/390
[58] Field of Search ................................. 128/284–287

[56] References Cited

U.S. PATENT DOCUMENTS

| | | | |
|---|---|---|---|
| 3,610,244 | 10/1971 | Jones, Sr. | 128/287 |
| 3,776,234 | 12/1973 | Hoey | 128/287 |
| 3,794,038 | 2/1974 | Buell | 128/287 |
| 3,810,472 | 5/1974 | Aldinger et al. | 128/287 |
| 3,848,594 | 11/1974 | Buell | 128/284 |

*Primary Examiner*—John D. Yasko

[57] ABSTRACT

A diaper fastener which comprises tape and has first and second anchoring portions and an attachment portion. The first and second anchoring portions are secured, respectively, to the inner and outer surfaces of the diaper adjacent a lateral margin and each is in a force-transmitting relation to the attachment portion. The attachment portion has a pressure-sensitive adhesive disposed on one surface thereof, whereby it is securable to a remote region of the diaper for retaining the diaper on the wearer.

10 Claims, 4 Drawing Figures

DISPOSABLE DIAPER

This application is a division of my copending application Ser. No. 410,375, filed Oct. 29, 1973 now U.S. Pat. No. 4,100,921.

BACKGROUND OF THE INVENTION

This invention relates to fasteners for securing diapers to the human body. The fasteners of the present invention are particularly suitable for use with disposable diapers comprising an absorbent body and a water impervious backing sheet.

While a number of pressure-sensitive tape fasteners for disposable diapers have been proposed, one or more of various deficiencies in each of these prior designs has led to both manufacturing and consumer use problems. Typical of such deficiencies are inadequate anchoring of the fastener to the diaper, anchoring in such a way as to place undue strain on various diaper portions, the use of release sheets which must be separately disposed of, the presence of fastener portions which project from the diaper rendering manufacturing and packaging difficult and giving the end product an unaesthetic appearance, etc.

SUMMARY OF THE INVENTION

In view of the foregoing, it is a principal object of the present invention to provide a diaper fastener which overcomes the deficiencies noted above. It is a further object to provide such a fastener which is relatively inexpensive to manufacture and to apply to the actual diaper during the manufacture of the diaper.

These and other objects are achieved by providing a fastener which comprises tape having first and second anchoring portions and an attachment portion. The first and second anchoring portions are secured, respectively, to the inner and outer surfaces of the diaper adjacent a lateral margin thereof. Each anchoring portion is in a force-transmitting relation to the attachment portion. The attachment portion has a pressure-sensitive adhesive disposed on one surface thereof, whereby it is securable to a remote region of the diaper for retaining the diaper on the wearer. In preferred embodiments of the invention the second anchoring portion is integral with the attachment portion; the first anchoring portion is adhesively secured to the attachment portion; and the attachment portion is, prior to use of the fastener by the consumer, folded back with its adhesive-bearing surface in contact with the outer, exposed surface of the first anchoring portion.

In another aspect of the invention such a fastener comprises first and second pieces of tape each having a first surface with an adhesive disposed thereon and a second surface which is free of adhesive. A major portion of the first tape first surface is adhesively secured to an inner surface of the diaper, and a minor portion of that surface is adhesively secured to a minor portion of the second tape first surface. Another portion of the second tape first surface is releasably secured to the first tape second surface, whereby it may be peeled from the first tape second surface and then secured to another portion of the diaper to secure the diaper to the diaper wearer.

BRIEF DESCRIPTION OF THE DRAWING

Other objects, features, and advantages of the invention will appear from the following description of particular preferred embodiments taken together with the accompanying drawings in which.

DETAILED DESCRIPTION OF PARTICULAR PREFERRED EMBODIMENTS

Figure 1:
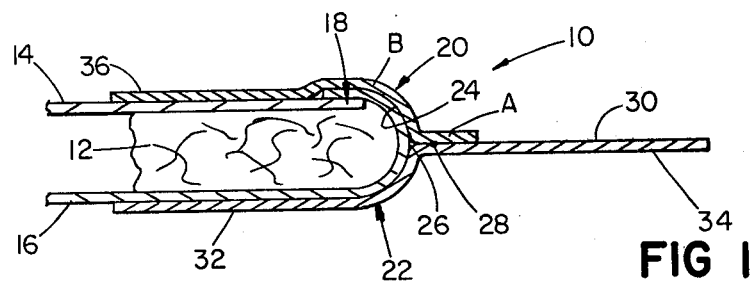
FIG. 1 is a sectional view taken through a fastener constructed according to the invention and the adjacent portion of the diaper itself with the fastener attachment portion projecting from the diaper in readiness for securing the diaper to an infant.
Figure 2:
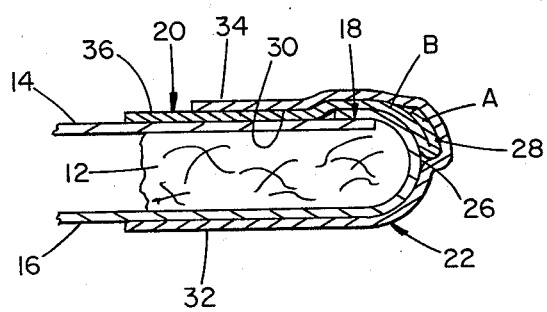
FIG. 2 is a view similar to FIG. 1 with the attachment portion folded back onto other portions of the fastener.

The fasteners to be described are typically applied near the corner of a rectangular disposable diaper overlapping the diaper's lateral margin. While the fastener may be beneficially used with diapers of virtually any construction and configuration, an especially desirable overall product is achieved when the fastener is employed on a conventional box-pleat diaper. Referring to FIGS. 1 and 2, there is shown a fastener 10 secured adjacent the lateral margin of a diaper which comprises an absorbent body 12 sandwiched between an inner, water pervious liner 14 (e.g., a nonwoven fabric) and a flexible, water impervious backing sheet 16 (e.g., 1 mil polyethylene). The backing sheet 16 bends around the lateral edge of the absorbent body 12 and overlies, for a short lateral distance, the liner 14, as at 18. The backing sheet 16 is secured to the liner 14 in this region 18 (e.g., as by heat sealing).

The fastener itself comprises a first strip of tape 20 and a second strip of tape 22. The strip of tape 20 is secured to inner surfaces of the diaper comprising portions of the diaper's liner 14 and the backing sheet 16. It may be so secured by means of a pressure-sensitive adhesive which entirely covers a first surface 24 of the tape strip 20. The strip 20 projects beyond the lateral edge 26 of the diaper and is secured to the tape strip 22, as at 28, by means of the adhesive on surface 24 which contacts the tape 22.

The tape strip 22 also has an adhesive entirely coating one surface 30. The portion 32 of strip 22 to the left of the region 28 in FIGS. 1 and 2 is a second anchoring portion of the fastener 10 while the portion 34 to the right of the region 28 may be termed an attachment portion. The anchoring portion 32 is firmly secured to the backing sheet 16 by means of the adhesive on surface 30. In the region 28 the adhesives 24 and 30 are in a face-to-face configuration, firmly securing the tape strip 20 to the tape strip 22, so as to be in a force-transmitting relation to the attachment portion 34.

The fastener 10 in its unfolded configuration (FIG. 1), in a cross section taken longitudinally through the fastener, is thus in the form of a "Y" with the two upper arms of the "Y" serving as anchoring portions of firmly secure the fastener to the diaper on both the inner and the outer faces of the diaper. Furthermore, with the anchoring portion 20 secured to the liner 14 as well as the backing sheet 16, the stress exerted by the fastener 10 upon the diaper will be more uniformly transmitted to the component parts of the diaper and will thereby be less likely to cause undesirable stretching, and ultimate tearing, of the plastic backing sheet 16.

Furthermore, with this construction the portion of tape strip 20 lying between locations A and B in FIG. 1 will be the part of the fastener 10 facing the wearer's skin at the location where the diaper's front and back waistline portions are to be secured by the fastener 10. There will thus be a non-adhesive surface in this critical region and unintentional contact of adhesive with the wearer's skin, either during application of the diaper or during use as various diaper portions become twisted and shifted by body movements, will be much less likely to occur.

Referring to FIG. 2, it can be seen that the diaper, as packaged and as initially presented to the consumer, has no projecting fastener portions. The attachment portion 34 is folded over so that its adhesive surface is in contact with the second, non-adhesive surface 36 of the tape strip 20. The surface 36 is preferably treated in any conventional fashion to resist tenacious bonding by the adhesive 30. The resultant light bonding will be sufficient to maintain the attachment portion 34 in the configuration shown in FIG. 2 during manufacture and packaging but will permit the easy peeling back of the attachment portion 34 by the consumer to achieve the configuration shown in FIG. 1 at the time the diaper is to be applied to the infant.

Figure 3:
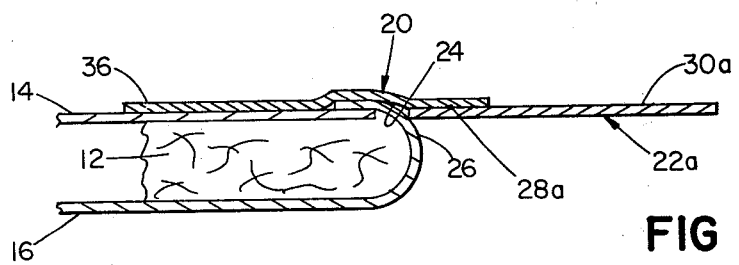
FIG. 3 is a view similar to FIG. 1 of an alternative embodiment of the invention.
Figure 4:
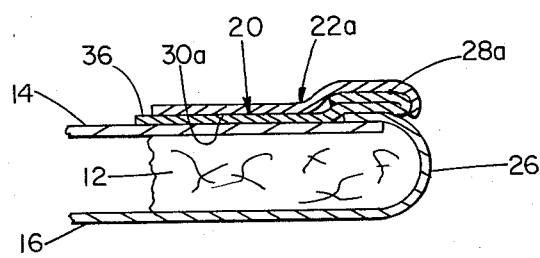
FIG. 4 is a view similar to FIG. 3 with the fastener attachment portion folded back for packaging.

An alternative embodiment is illustrated in FIGS. 3 and 4. In this embodiment the portions of the diaper itself and the strip of tape 20 are identical with the construction shown in FIGS. 1 and 2. The second strip of tape 22a, however, is not secured directly to the diaper but only to the strip 22 in the region 28a which comprises a minor portion of the adhesive bearing surfaces 24, 30a, respectively, of the tapes. As shown in FIG. 4, the "storage" of the tape 22a by contacting the adhesive 30a with the treated surface 36 of tape 20 is identical to that shown in the embodiment of FIGS. 1 and 2.

The embodiment of FIGS. 3 and 4 thus foregoes one of the benefits of the embodiment of FIGS. 1 and 2 (i.e., the unusually secure anchoring of the fastener to the diaper) while achieving the remainder of the benefits in a construction which is somewhat simpler and more inexpensive to manufacture and to apply to the diaper.

While particular preferred embodiments of the present invention have been illustrated in the accompanying drawings and described in detail herein, other embodiments are within the scope of the invention and the following claims.

I claim:

1. A tape fastener system in combination with a disposable diaper of the type which comprises an absorbent core interposed between a fluid-pervious body-contacting cover sheet and a fluid-impervious backing sheet, said tape fastener system comprised of a composite tape formed from two strips of flexible sheet material coated with pressure-sensitive adhesive on one surface and a release coating on the other surface, said strips being longitudinally aligned and joined to each other at a narrow zone of overlap with the adhesive surfaces of the overlapped strips being in contact at the zone of overlap to form a permanent bond, one end portion of the composite tape adjacent the overlap zone having its adhesive disposed on the face of the composite tape opposite from that face of the composite tape on which the adhesive of the other end portion is disposed, the first end portion of said composite tape being secured by said adhesive to the cover sheet of said diaper at one corner adjacent the diaper edge, and the second end portion of said composite tape being adapted to extend beyond the edge of the diaper for use in fastening the diaper around the waist.

2. The tape fastener system of claim 1 wherein the second end portion of said composite tape is folded transversely at the diaper edge into over-lying position over said first end portion with the adhesive face of said second end portion releasably adhered to the release coated surface of the first end portion.

3. The tape fastener system of claim 1 wherein said transverse fold is disposed at the edge of said overlap.

4. The tape fastener system of claim 3 wherein said transverse fold and the edge of said overlap are disposed outboard of the associated diaper edge.

5. The tape fastener system of claim 3 wherein said transverse fold and the edge of said overlap are disposed inboard of the associated diaper edge.

6. A tape fastener system in combination with a disposable diaper to the type which comprises an absorbent core interposed between a fluid-pervious body-contacting cover sheet and a fluid-impervious backing sheet, said tape fastener system comprised of a composite tape formed from two strips of flexible sheet material coated with pressure-sensitive adhesive on one surface, said strips being longitudinally aligned and joined to each other at a narrow zone of overlap with the adhesive surfaces of the overlapped strips being in contact at the zone of overlap to form a permanent bond, one end portion of the composite tape adjacent the overlap zone having its adhesive disposed on the face of the composite tape opposite from that face of the composite tape on which the adhesive of the other end portion is disposed, the first end portion of said composite tape being secured by said adhesive to the cover sheet of said diaper at one corner adjacent the diaper edge and being coated with a release coating on the other surface thereof, and the second end portion of said composite tape being adapted to extend beyond the edge of the diaper for use in fastening the diaper around the waist.

7. The tape fastener system of claim 6 wherein the second end portion of said composite tape is folded transversely at the diaper edge into over-lying position over said first end portion with the adhesive face of said second end portion releasably adhered to the release coated surface of the first end portion.

8. The tape fastener system of claim 7 wherein said transverse fold is disposed at the edge of said overlap.

9. The tape fastener system of claim 8 wherein said transverse fold and the edge of said overlap are disposed outboard of the associated diaper edge.

10. The tape fastener system of claim 8 wherein said transverse fold and the edge of said overlap are disposed inboard of the associated diaper edge.

* * * * *